United States Patent [19]

Balding et al.

[11] Patent Number: 4,752,289
[45] Date of Patent: Jun. 21, 1988

[54] INFUSION APPARATUS

[75] Inventors: Alan S. Balding; Nigel F. Carter; Paul F. Frampton; Vincent A. Rosso, all of Oxfordshire, England

[73] Assignee: Vi-Tal Hospital Products Ltd., Reading, England

[21] Appl. No.: 840,387

[22] Filed: Mar. 17, 1986

[30] Foreign Application Priority Data

Mar. 20, 1985 [GB] United Kingdom ............... 8507210
May 1, 1985 [GB] United Kingdom ............... 8511036

[51] Int. Cl.⁴ .......................................... A61M 1/00
[52] U.S. Cl. .................................. 604/118; 604/67; 604/245; 128/DIG. 13; 340/573
[58] Field of Search ............... 604/50, 65, 67, 118, 604/121, 245, 66; 128/675, 748, DIG. 13; 73/726, 730; 340/573, 516, 562, 501

[56] References Cited

U.S. PATENT DOCUMENTS

| | | | |
|---|---|---|---|
| 3,818,765 | 6/1974 | Eriksen | 128/675 |
| 4,116,075 | 9/1978 | Ort | 73/726 |
| 4,148,314 | 4/1979 | Yin | 604/118 |
| 4,184,491 | 1/1980 | McGannon | 604/118 |
| 4,277,227 | 7/1981 | Jenkins | 604/118 |
| 4,326,519 | 4/1982 | D'Alo et al. | 604/177 |
| 4,398,542 | 8/1983 | Cunningham et al. | 604/118 |
| 4,457,751 | 7/1984 | Rodler | 604/67 |
| 4,526,574 | 7/1985 | Pekkarinen | 604/118 |

Primary Examiner—C. Fred Rosenbaum
Assistant Examiner—Mario Costantino
Attorney, Agent, or Firm—Jeffers, Hoffman & Niewyk

[57] ABSTRACT

An infusion pump pressure monitor comprises a drive (26, 27, 30, 31) for an infusion pump, a pressure sensor (38) to monitor the delivery pressure downstream of the pump, and a programmed computer (34, 35). The computer (34, 35) is programmed to monitor the maximum delivery pressure that occurs during an initial operating period, and then, subsequently to monitor the delivery pressure downstream of the pump for the remainder of the delivery period of the infusion pump. The programmed computer (34, 35) is programmed to disable the drive (26, 27, 30, 31) for the infusion pump if the monitored delivery pressure differs by more than a predetermined amount from the maximum pressure monitored during the initial operating period. The infusion liquid is carried by a disposable infusion set having a pressure responsive chamber (1) located in a key-hole shaped slot (44) in the pressure monitor.

6 Claims, 6 Drawing Sheets

INFUSION APPARATUS

BACKGROUND OF THE INVENTION

This invention relates to apparatus for the infusion of medical liquids into patients and is particularly concerned with infusion sets and pressure monitors which are used with infusion pumps. Frequently it is required that particular medical liquids be infused into the body of a patient at a predetermined rate. It is possible for the tube of an infusion set leading to the patient to be kinked, or get blocked, and, under these circumstances, firstly the medical liquid is no longer infused into the patient which is the first source of danger but, perhaps more importantly, if the tube is subsequently unkinked or the blockage suddenly released a large quantity of the medical liquid is suddenly infused into the patient as a result of the build up of pressure in the kinked or blocked tube. Such a sudden surge of medical liquid into the patient can be life threatening, particularly in the case of some drugs.

It is therefore desirable to provide some form of automatic infusion pressure monitor which monitors the pressure of the medical fluid in an infusion set or tube leading to the patient. Previously such infusion pressure monitoring devices have included a pressure sensor and means to compare the sensed pressure with a preset value corresponding to the maximum allowed delivery pressure. The delivery pressure for an infusion varies with a number of factors such as the viscosity of the medical fluid, the cross sectional area of the needle through which the infusion is performed, the speed at which the infusion of medical fluid is to be introduced into the patient and whether a filter is included in the infusion line. Conventional infusion pressure monitoring devices which include a preset maximum pressure limit typically have their maximum pressure limit set to a value higher than is likely to be encountered with, for example, a high viscosity medical liquid being pumped at a high rate through a filter and fine needle. When such a device is subsequently used with less viscous medical liquids at lower pumping rates through coarser needles the monitoring device is relatively insensitive and so only responds if the infusion tube is completely blocked for a considerable period of time.

Infusion pressure monitoring devices are also available in which an operator sets manually the required maximum delivery pressure. Naturally such devices are subject to human error and, even more importantly, there is a tendency for the operator to set the maximum infusion pressure to a high value so that the operator is not troubled by "false alarms".

SUMMARY OF THE INVENTION

According to a first aspect of this invention an infusion pump pressure monitor comprises means to drive an infusion pump, a pressure sensor to monitor the delivery pressure downstream of the pump, and a programmed computer programmed to monitor the maximum output of the sensor and hence the maximum delivery pressure that occurs during an initial operating period, and then, subsequently to monitor the output of the sensor and hence the delivery pressure downstream of the pump for the remainder of the delivery period of the infusion pump, the programmed computer being programmed to disable the means to drive the infusion pump if the monitored delivery pressure differs by more than a predetermined amount from the maximum pressure monitored during the initial operating period.

The initial operating period of any infusion is usually initiated and monitored by medically qualified personnel and accordingly, during this initial operating period the monitoring device may not act to disable the means to drive the infusion pump. However, it is very much preferred that the device includes a memory programmed with both high and low pressure default values and the programmed computer is programmed to compare the monitored output of the pressure sensor with the high and low pressure default values and to disable the means to drive the infusion pump if the monitored delivery pressure is outside the range defined by the high and low pressure default values during this initial operating period.

Preferably the pressure sensor is arranged to provide an averaged value of the delivery pressure. This smooths the instantaneous changes in the delivery pressures that occur and prevents any short term transient effects generating false alarms. Preferably, the programmed computer derives from the maximum averaged monitored delivery pressure a maximum and minimum acceptable delivery pressure. The maximum and minimum acceptable delivery pressure values are then loaded into the memory and then, subsequently, after the initial operating period, the programmed computer compares the averaged monitored pressure with the values stored in the memory. If the averaged monitored value falls within the range defined by the maximum and minimum acceptable delivery pressure values and also falls within the range defined by the maximum and minimum default pressure values then the infusion is allowed to proceed. If not, the means to drive the infusion pump are disabled.

The programmed computer is preferably programmed to perform its derivation of maximum and minimum acceptable delivery pressures automatically each time that the device is actuated and on each occasion that the delivery speed of the infusion pump is varied. Preferably the device not only disables the infusion pump drive but also triggers an alarm to notify medical personnel that the infusion has stopped.

According to a second aspect of this invention a liquid infusion set for use in infusing a medical liquid into a patient includes a pressure responsive chamber to enable the infusion pressure of the medical liquid to be monitored during infusion by an associated pressure sensor, the pressure responsive chamber comprising a substantially rigid, hollow housing having a flanged end face, and a resilient flexible diaphragm connected to the flange and covering the end face, the housing also having a liquid inlet and a liquid outlet passage in communication with the inside of the housing and hence in communication with an inside face of the diaphragm, the liquid inlet and outlet passage being mutually orthogonal with one of them extending substantially normally away from the diaphragm, in use, the flanged end of the housing co-operating with a keyhole-shaped slot in the pressure sensor to associate the diaphragm with a sensing element, and the said one of the inlet and outlet passage providing at least part of finger gripping means to enable the pressure responsive chamber to be manoeuvred into the keyhole-shaped slot of the pressure sensor.

Preferably the flanged end of the housing is circular and the flange forms the outer extremity of a dished face. In this case the housing preferably also includes a hollow box-like portion opening into the dished face and extending in a direction away from the diaphragm. The inlet passage opens into one end of the hollow box-like portion and the outlet passage opens into the other end of the hollow box-like portion remote from the diaphragm.

Preferably a circular skirt is connected to the external surface of the dished face and extends away from the diaphragm. The skirt preferably forms an integral part of the end faces of the rectangular box-like portion and additional reinforcing webs may be provided extending between the inside of the skirt and the sides of the rectangular box-like section.

Preferably the finger-gripping means also includes an additional web extending between the said one of the inlet and outlet passage and the rear face of the box-like portion of the housing, the web being generally rectangular in shape. This web firstly buttresses the connection between the said one of the inlet and outlet passage and the remainder of the housing and also provides a convenient tab to be held by an operator when inserting the pressure responsive chamber into the pressure sensor. Preferably the generally rectangular web is formed with a serpentine or ribbed configuration so that it can be gripped more easily.

Preferably the infusion set also includes tubing connecting the inlet passage to a Luer-lock connector so that it can be associated with the outlet of a conventional infusion syringe. The infusion set preferably further includes microbore tubing connecting the outlet passage to a Luer-lock connector for attachment to an infusion needle assembly. The infusion set may also include an additive Y site through which additional medical liquid can be injected into the infusion set and may include a filter.

Preferably the infusion set is used with a pressure monitor in accordance with the first aspect of this invention and, in this case, the pressure monitor includes a load surface and includes a key-hole shaped slot, the housing of the infusion set is engaged in the key-hole shaped slot with the resilient flexible diaphragm resting against the load surface of the pressure sensor to enable the pressure within the infusion set to be transmitted to the load surface. In this way the delivery pressure of the medical liquid to be infused into the patient is transmitted through the flexible diaphragm of the infusion set to the load surface. There is no possibility of the load surface or any other part of the pressure monitor coming into contact with and in any way contaminating the medical liquid to be infused into the patient. Preferably the load surface is located at the free end of a cantilevered beam, and, in this case, the beam has strain gauges fixed to it to complete the sensing element and to enable the degree of bending of the beam, and hence the pressure within the infusion set to be monitored.

It may be desirable to ensure that the diaphragm is correctly positioned with respect to the load surface. Accordingly, the pressure monitor may include a switch which is actuated only when the housing of the infusion set is correctly positioned, to prevent actuation of the infusion pump unless the switch is actuated.

By use of a monitoring device in accordance with this invention the infusion pump is automatically stopped and an alarm given if the inlet or outlet from the system becomes in any way occluded or restricted. The automatic setting of the points at which the monitoring device stops the infusion pump and raises an alarm in accordance with the maximum pressure that occurs during an initial operating periods, naturally takes account of the viscosity of the medical liquid being infused, the inherent back pressure of the system which is of course dependent upon the size of needle and the presence of any filters in the tubing leading to the patient, and the rate at which the infusion pump has been set to deliver the medical fluid to the patient. The default settings protect the system from any gross pressure excursions during the initial, or learning, phase of its operation and, are, in any event, effective irrespective of the "learnt" acceptable maximum and minimum pressure values that are set into the memory of the device as a result of its initial operating period. Thus, if during the infusion, the system parameters change, for example as a result of the infusion tube being kinked, being blocked, or a filter associated with the tubing being blocked or, for example, if the tubing becomes disconnected from either the infusion pump or from the infusion needle, or some unexpected variation in the output of the infusion pump takes place then, the infusion pump is stopped and an alarm raised. The monitoring device in accordance with the present invention is substantially foolproof in operation since it does not rely on any human intervention to set its parameters and it provides a much closer control over the allowed infusion delivery pressure. Further since the pump is stopped and an alarm given if the output pressure falls below a value derived from the pressure occurring during the initial learing period the device in accordance with this invention identifies failures of the system such as a blockage upstream of the pump or disconnection of the tubing set that are not identifiable with the conventional monitoring devices.

BRIEF DESCRIPTION OF THE DRAWINGS

A particular example of a pressure monitor and infusion set in accordance with this invention will now be described with reference to the accompanying drawings in which.

DESCRIPTION OF PREFERRED EXAMPLE

Figure 1:
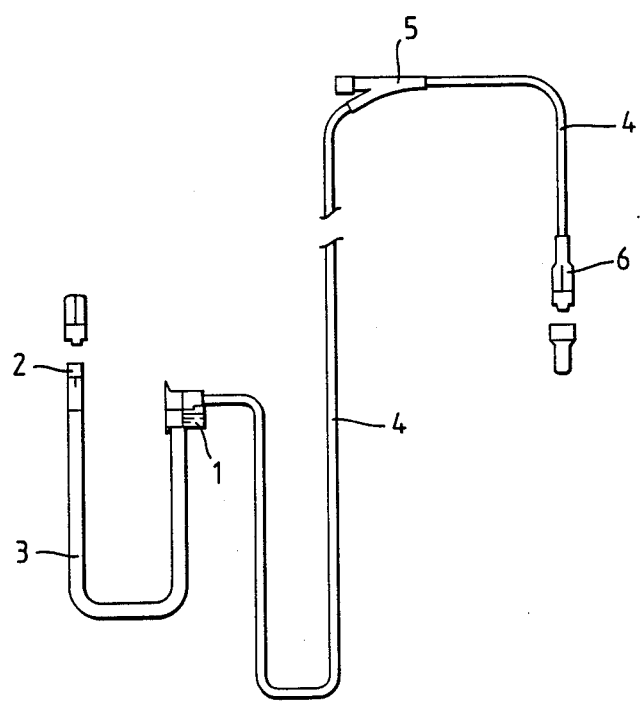
FIG. 1 is a diagram of an infusion set.
Figure 2:
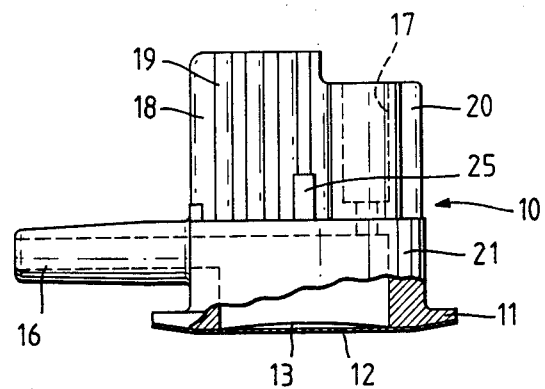
FIG. 2 is a partly sectioned side elevation of the pressure responsive chamber.

In this example a disposable infusion set includes a pressure responsive chamber 1 which is connected to a Luer-lock connector 2 by inlet tubing 3. The pressure responsive chamber 1 is connected via kink resistant small bore tubing 4 to an additive Y-site 5 and thence to a Luer-lock connector 6 which, in use, is connected to an infusion needle assembly inserted in a patient.

Figure 3:
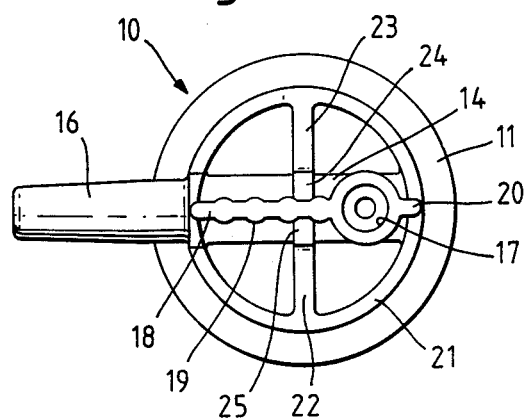
FIG. 3 is a plan of the pressure responsive chamber.
Figure 4:
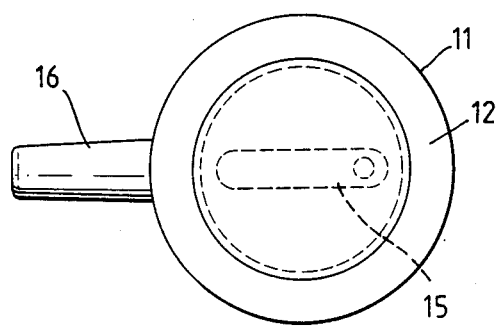
FIG. 4 is an underplan of part of the infusion tubing set.

The pressure responsive chamber 1 comprises a substantially rigid circular housing 10 with an annular bevelled edge flange 11 at one end. A resilient thin flexible diaphragm 12 is welded onto the flange and extends across the end face of the housing 10. The inside of the housing is dished to provide a chamber of small volume betwen the diaphragm 12 and the dished face 13. The housing also includes a generally rectangular box-like portion 14 showing most clearly in FIGS. 3 and 4 which communicates with the dished shaped face 13 via an oval opening 15.

An inlet passage 16 communicates with one end of the box-like portion 14 and an outlet passage 17 communicates with the other end of the box-like portion 14. The outlet passage 17 and inlet passage 16 are mutually orthogonal with the outlet passage 17 being substantially normal to the diaphragm 12. A generally rectangular finger-gripping tab 18 extends between the outlet passage 17 and the base of the rectangular box-like portion 14. The surface of the tab 18 includes a number of ribs 19 so that it is easier to grip, in use. An additional rib 20 is provided at the side of the outlet passage 17 remote from the tab 18 to further extend the finger-gripping tab.

A circular skirt 21 surrounds and extends rearwards away from the flanged end 11 to stiffen the housing. This skirt 21 is attached via reinforcing webs 22 and 23 to the box-like portion 14. The stiffening webs 22 and 23 include extensions 24 and 25 which buttress the rectangular finger-gripping portion 18 and provide further means for engagement between the fingers of the user and the chamber. The pressure responsive chamber has a very low volume and this, together with the small bore tubing 4 leads to a very low priming volume for the entire infusion set. The arrangement of the inlet and outlet tube, together with the web 18 provides a strong robust and substantially rigid housing which can be easily gripped and manoeuvred by an operator into its associated pressure monitor in use.

Figure 5:
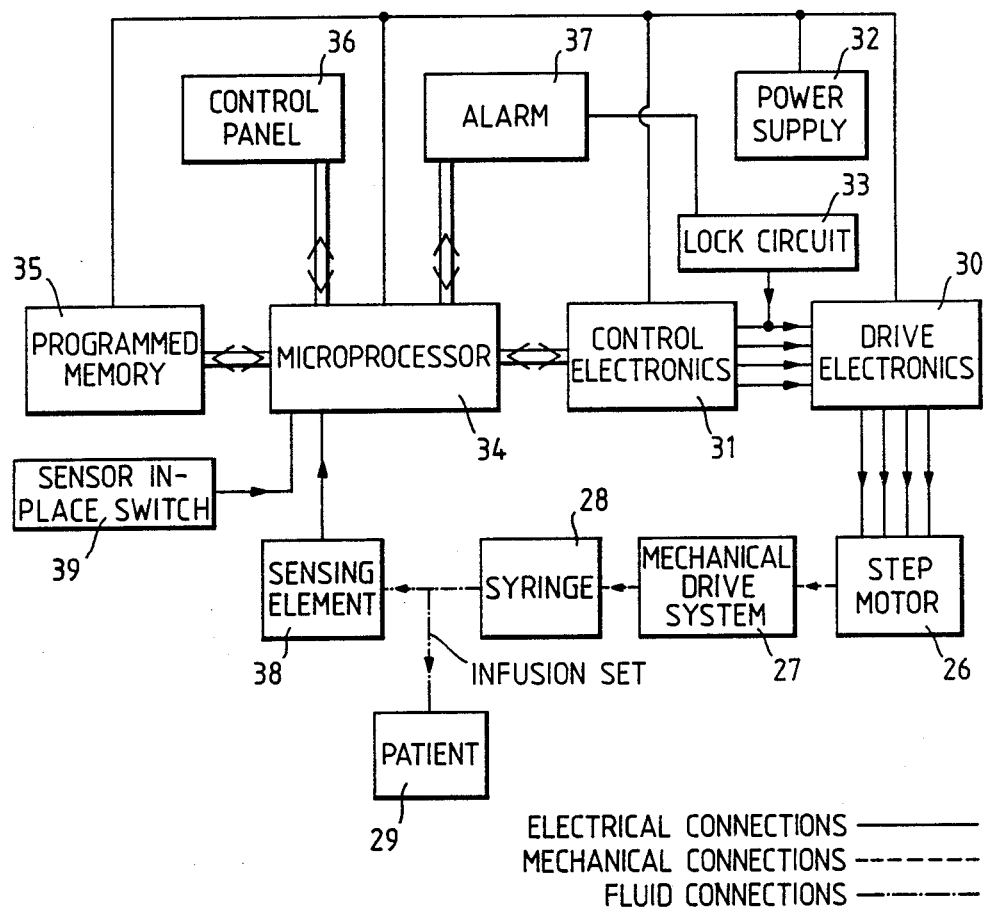
FIG. 5 is a block diagram of the overall system.
Figure 6:
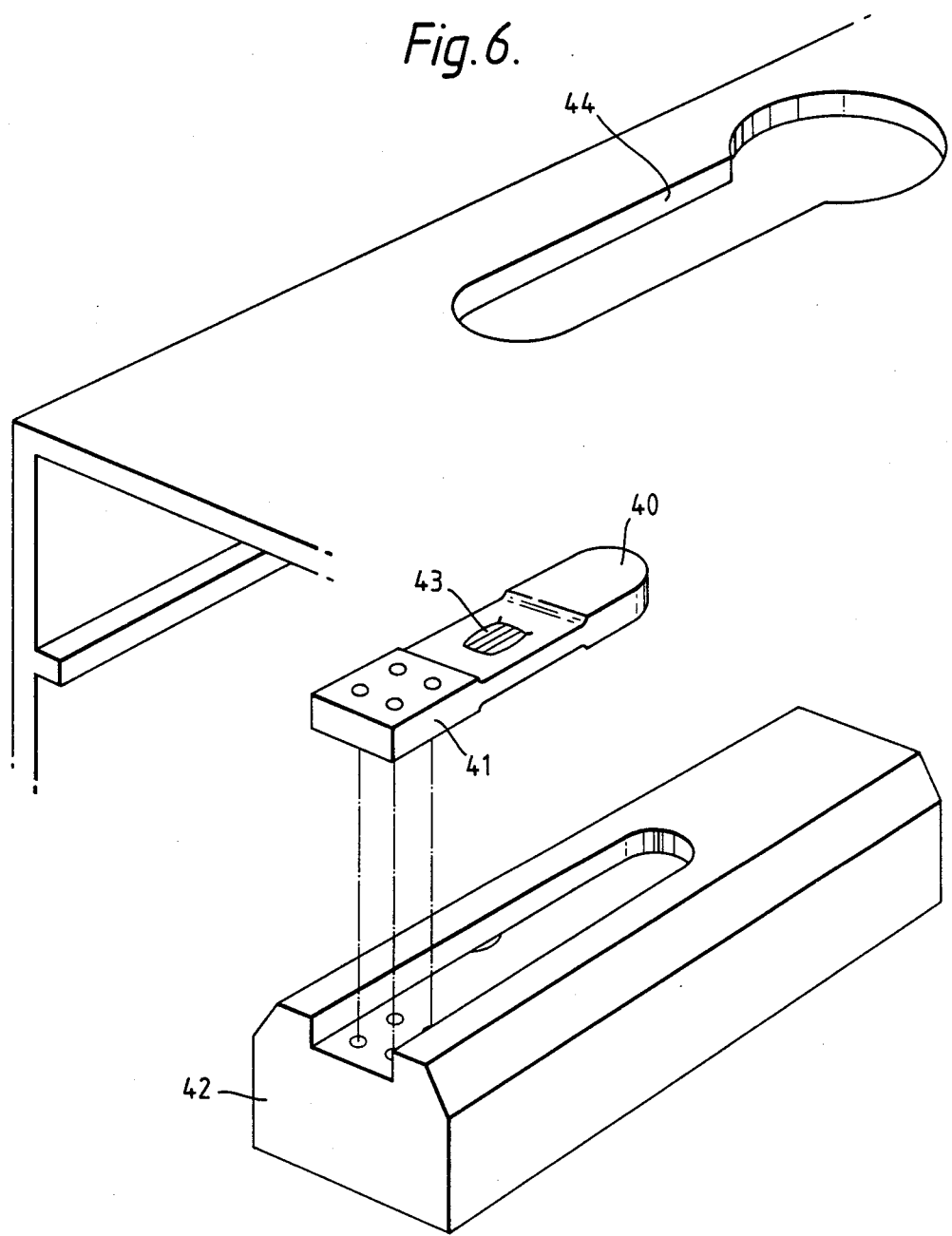
FIG. 6 is an exploded perspective view of part of the pressure sensor.

This example of pressure monitor forms part of an infusion driver which holds a syringe filled with medical liquid and actuates the plunger of the syringe to discharge the medical liquid from the syringe through the infusion set and into the patient. The majority of the infusion syringe driver is conventional in construction and is shown generally in FIG. 5. In FIG. 5 the solid lines indicate electrical connections; the dotted lines indicate mechanical connections; and, the chain-dotted lines indicate liquid connections. The infusion pump includes a stepper motor 26 which, via a mechanical drive system 27, drives a syringe 28 which leads into the infusion set already described connected to the patient 29. The stepper motor 26 is driven by an electronic drive circuit 30 which in turn leads to a power supply 31, an electronic control circuit 32 and a lock circuit 33. The electronic control circuit 31 is driven by a microprocessor 34 which is also linked to a programmed memory 35 a control panel 36 for entering the required infusion rate, and an alarm 37. The alarm 37 is also linked to the lock circuit 33. An input from a pressure sensing element 38 and from a switch 39 which detects when the infusion set is correctly located in the pressure monitor are also fed to the microprocessor 34.

The pressure sensing element 38 comprises a load surface 40 located at the free end of a cantilevered aluminum beam 41, the other end of which is fixed to a support block 42. The cantilevered beam 41 includes a bending portion having a reduced thickness with a pair of strain gauges 43 bonded on opposite sides of it. A case for the pressure monitor includes a keyhole-shaped slot 44 located above the pressure sensor and the flange 11 of the pressure responsive chamber of the infusion set is introduced into the enlarged end of the keyhole-shaped slot 44 and then moved along the parallel-sided portion so that the flange 11 is retained by the sides of the keyhole-shaped slot 44. In this position, the flexible diaphragm 12 engages the load surface 40 of the beam 41 so that pressure of liquid inside the chamber 1 bears agnast the free end of the aluminium beam 41 and causes a bending of the beam 41 corresponding to the pressure of the liquid inside the chamber 1.

Figure 7:
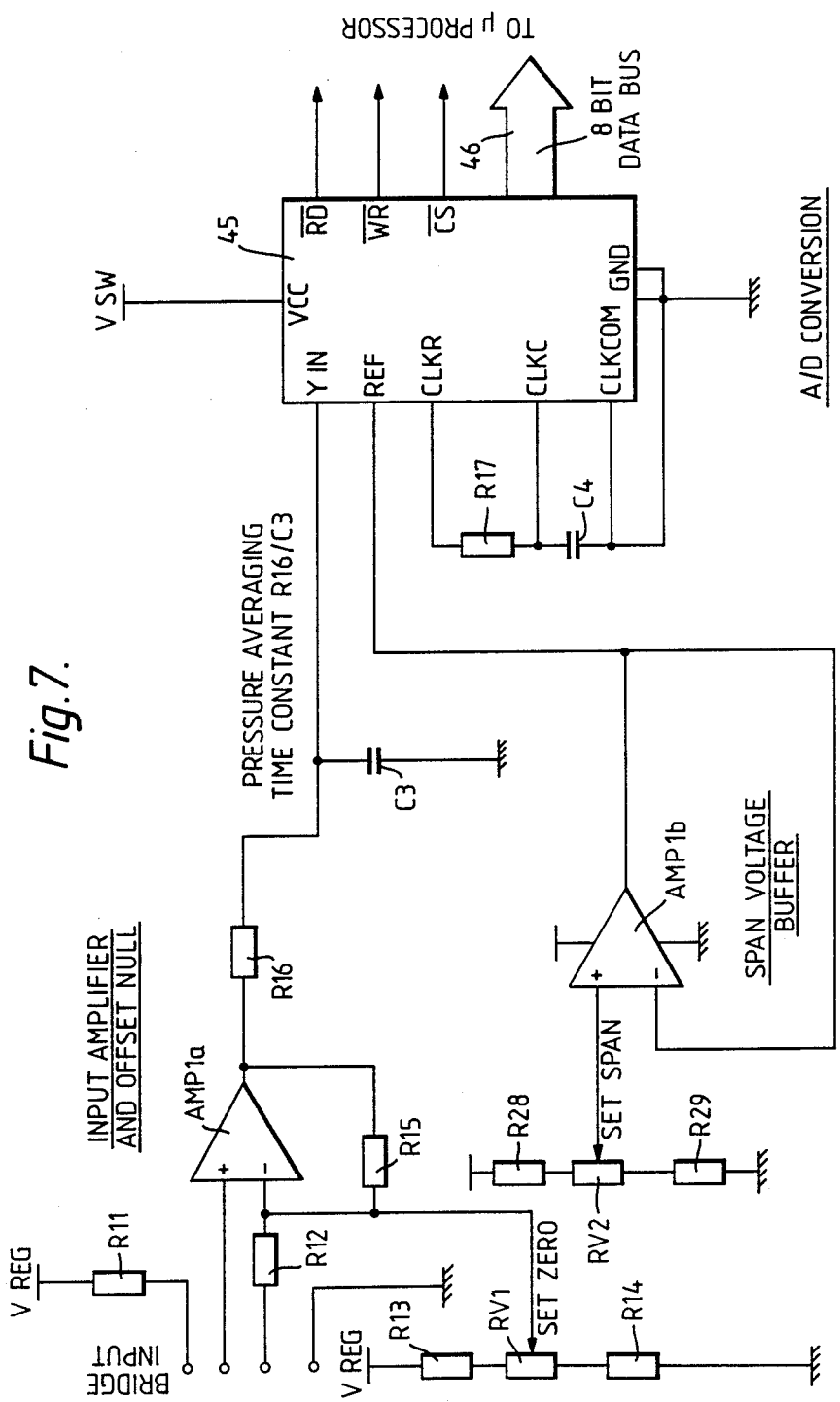
FIG. 7 is a circuit diagram of a strain gauge bridge interface circuit; and,
FIG. 8 is a flow diagram of a computer program.

The two strain gauges 43 are connected together in a bridge circuit which is in turn connected across the input of a differential operational amplifier AMP1$a$ as shown in FIG. 7. The negative going input of the amplifier AMP1$a$ is also connected to a resistance chain formed by fixed resistors R13 and R14 and variable resistor RV1 to provide a zero setting adjustment to compensate for any slight differences in the strain gauges 43. The output that is supplied to the differential amplifier AMP1$a$ is an indication of the degree of bending of the beam 41 and hence of the pressure of the liquid in the chamber 1. This difference is amplified in the amplifier AMP1$a$ and then averaged by the resistor capacitor network R16 C3 before being fed to the analogue input of an analogue to digital converter 45. A span voltage buffer including resistor chain R28 RV2 R29 and differential amplifier AMP1$b$ is connected to the reference input of the analogue to digital converter 45. A digital output corresponding to the pressure of the infusion fluid is fed via an 8 bit data bus 46 to the microprocessor 34.

Figure 8:
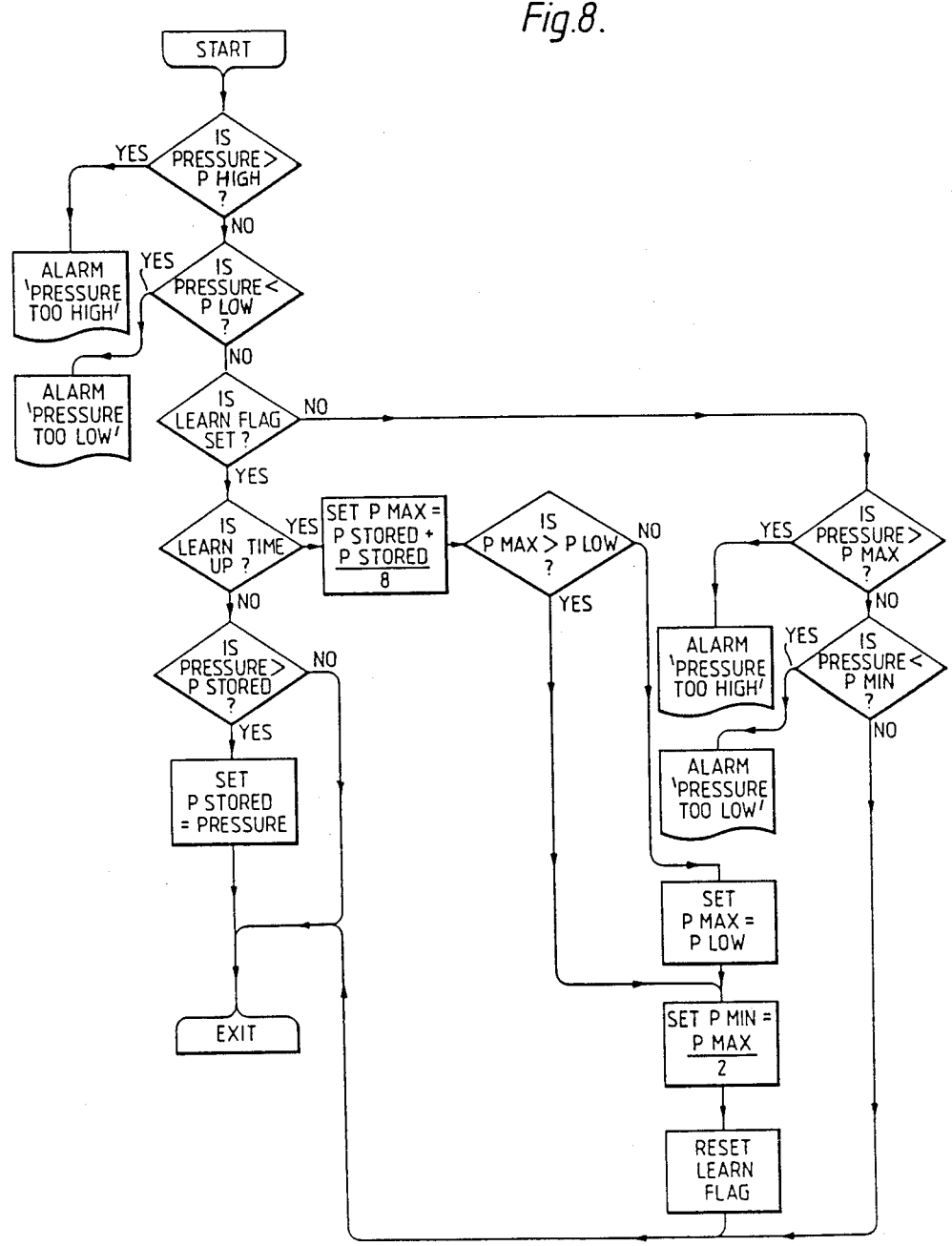

The microprocessor 34 is programmed to monitor the output of the analogue to digital converter 45 and hence monitor the pressure of the infusion liquid at regular intervals, at least before each delivery interval of the infusion pump. The microprocessor 34 is also programmed to set a learn flag each time the device is initially actuated and each time the rate of the infusion is changed. Then, the microprocessor goes through the program shown in FIG. 8 at each monitoring interval. Assuming that the infusion pump has just been started the learn flag is set and the first question that is asked is whether the pressure currently being monitored and thus the current output of the analogue to digital converter 45 is greater than a previously stored high default value $P_{high}$. If it is, then the alarm 37 is triggered and the drive 30 for the infusion pump is disabled. The next question is whether the pressure currently being monitored is less than a previously stored low default value $P_{low}$. If it is, then the alarm 37 is triggered and the drive 30 for the infusion pump is disabled.

Then, as the learn flag is set, the following question is whether the pressure currently being monitored is greater than any pressure stored in the memory of the microprocessor. Assuming that it is then the subsisting pressure is entered into the memory of the microprocessor and this completes the checking routine. At each subsequent monitoring interval during an initial learning time the instantaneous pressure is again checked against the stored pressure value and, if the instantaneous pressure is greater than the stored value this instantaneous pressure is used to replace the previously stored value with an updated value. Accordingly, at the end of the learning time the pressure stored in the memory of the microprocessor is a maximum averaged pressure that has occurred during the initial learning period.

At the next monitoring interval immediately after the learning time has expired, the program sets the acceptable maximum infusion pressure $P_{max}$ at a value equal to $$P_{max} = P_{stored} + (Pstored/8)$$

Thus, the maximum acceptable pressure for the remainder of the infusion is determined as being slightly greater than that which has occurred during the initial learning period. The computer then checks to ensure that the value of $P_{max}$ is greater than the initially set low default value for pressure $P_{low}$. If it is then a minimum acceptable value of $P_{min}$ is calculated as being equal to $$P_{min} = P_{max}/2$$

Once these values of $P_{max}$ and $P_{min}$ have been set the learn flag is unset before the routine is stopped. If $P_{max}$ is not greater than $P_{low}$ then $P_{max}$ is set to a value equal to $P_{low}$.

At the next monitoring interval since the learn flag is unset the program causes the microprocessor to compare the instantaneous pressure with both the values of $P_{max}$ and $P_{min}$. If the monitored pressure is between $P_{max}$ and $P_{min}$ the drive 30 for the infusion pump is enabled to infuse the required volume of liquid into the patient 29. If the pressure is greater than $P_{max}$ or less than $P_{min}$ the alarm 37 is triggered and the drive 30 for the infusion pump is disabled by ceasing the stepping signal and separately and continuously energising just one phase, effectively locking the stepping motor 26 in one position. Alternatively the infusion pump may be isolated from its power supply.

We claim:

1. A liquid infusion set for use in infusing medical liquid into a patient including a pressure responsive chamber; pressure sensing means; said pressure responsive chamber enabling infusion pressure of said medical liquid to be monitored during infusion by said pressure sensing means, said pressure responsive chamber comprising a substantially rigid, hollow, circular housing a, concave end face on said housing a flange surrounding and extending outwards away from said concave end face, a resilient flexible diaphragm having an inside face connected to said flange and covering said concave face and extending in a direction away from said diaphragm, a liquid inlet passage, and a liquid outlet passage, said inlet passage opening into one end of said hollow box-like portion and said outlet passage opening into the other end of said hollow box-like portion, said liquid inlet and outlet passages being in communication with the inside of sid hollow housing and hence in communication with said inside face of said diaphragm, said liquid inlet and outlet passages being mutually orthogonal with one of said liquid inlet and outlet passges extending substantially normally away from said diaphragm, a web extending between said one of said inlet and outlet passages and a rear face of said box-like portion of said housing remote from said diaphragm, said web being generally rectangular in shape, in use, said flanged end of said housing co-operating with a keyhole-shaped slot in said pressure sensing means to associate said diaphragm with a sensing element, and said one of said inlet and outlet passages and said web providing finger gripping means to enable said pressure responsive chamber to be maneuvered into said keyhole-shaped slot of said pressure sensing means.

2. An infusion pump pressure monitor and infusion set combination comprising a pressure monitor including drive means to drive an infusion pump, a housing including a key-hole-shaped slot, pressure sensing means located in said housing to monitor delivery pressure downstream of said pump, said pressure sensing means including a load surface, and a programmed computer operatively connected to said drive means and to said pressure sensing means, said computer including a memory and being programmed to monitor the maximum average output of said pressure sensing means and hence the maximum average delivery pressure that occurs during an intial operating period, to derive from said maximum average delivery pressure a maximum and minimum acceptable delivery pressure, said derived maximum and minimum acceptable delivery pressure, said derived maximum and minimum acceptable delivery pressures being loaded into said memory and said programmed computer subsequently, after said initial operating period, comparing the monitored average output of said pressure sensing means, and hence the delivery pressure downstream from the pump for the remainder of the delivery period, with said acceptable values stored in said memory, said programmed computer being programmed to disable said driving means unless said monitored average value falls within a range defined by said maximum and minimum acceptable delivery pressure values, and said infusion set including comprising a substantially rigid, hollow, circular housing, a concave end face on said housing, a flange surrounding and extending outwards away from said concave end face, a resilient flexible diaphragm having an inside face connected to said flange and covering said concave end face, a hollow box-like portion opening into said concave face and extending in a direction away from said diaphragm, a liquid inlet passage and a liquid outlet passage, said inlet passage opening into one end of said hollow box-like portion and said outlet passage opening into the other end of said hollow box-like portion, said liquid inlet and outlet passages being in communication with the inside of said hollow housing and hence in communication with said inside face of said diaphragm, said liquid inlet and outlet passages being mutually orthogonal with one of said liquid inlet and outlet passages extending substantially normally away from said diaphragm, a web extending between said one of said inlet and outlet passages and a rear face of said box-like portion of said housing remote from said diaphragm, said web being generally rectangular in shape, said housing of the infusion set being engaged in said key-hole shaped slot in said housing of said pressure sensing means with said resilient flexible diaphragm resting against said load surface of said pressure sensing means whereby said pressure within said infusion set is transmitted to said load surface of said pressure sensing means.

3. The combination according to claim 2, in which said pressure sensing means includes a cantilevered beam, strain gauges fixed to said cantilevered beam, said load surface bieng located at a free end of said cantilevered beam whereby the degree of bending of said cantilevered beam caused by said pressure within said infusion set causes said strain gauges to output a signal representative of said pressure within said pressure responsive chamber.

4. The combination of claim 2, in which said pressure monitor includes a switch, said switch being actuated only when said pressure responsive housing of said infusion set is correctly positioned in said key-holeshaped slot, to prevent actuation of said drive means unless said switch is actuated.

5. The combination according to claim 2, in which the infusion pump pressure monitor also includes a memory programmed with both high and low pressure default values and in which said programmed computer is programmed to compare said output of said pressure sensor with said high and low pressure default values and to disable said drive means if said monitored delivery pressure is outside a range defined by said high and low pressure default values during said initial operating period.

6. An infusion pump pressure monitor including: drive means to drive an infusion pump, a pressure sensing means to monitor delivery pressure downstream of said pump, and a programmed computer operatively connected to said drive means and to said pressure sensing means, said computer including a memory and having: means for monitoring the maximum average output of said pressure sensing means, means for determining the maximum average delivery pressure that occurs during an initial operating period, means for deriving from said maximum average delivery pressure a maximum and minimum acceptable delivery pressure as a multiple of 9/8 times substantially said maximum average delivery pressure, means for loading said derived maximum and minimum acceptable delivery pressures into said memory, means operable after the initial operating period for comparing the monitored average output of said pressure sensing means, and hence the delivery pressure downstream from the pump for the remainder of the delivery period, with said acceptable values stored in said memory, and means for disabling said driving means unless said monitored average value falls within a range defined by said maximum and minimum acceptable delivery pressure values.

* * * * *